United States Patent [19]

Reuther et al.

[11] 4,158,001

[45] Jun. 12, 1979

[54] TRIORGANOTIN COMPOUNDS OF HYDROXYDIAZENIUM OXIDES AND FUNGICIDAL USES THEREOF

[75] Inventors: Wolfgang Reuther, Ziegelhausen; Paul Raff, Ludwigshafen; Ernst-Heinrich Pommer, Limburgerhof; Hans-Peter Heidenreich, Frankenthal, all of Fed. Rep. of Germany

[73] Assignee: BASF Aktiengesellschaft, Fed. Rep. of Germany

[21] Appl. No.: 805,404

[22] Filed: Jun. 10, 1977

[30] Foreign Application Priority Data

Jul. 24, 1976 [DE] Fed. Rep. of Germany ....... 2633452

[51] Int. Cl.$^2$ .......................... A01N 9/20; B27K 3/34; C07C 111/00; C07C 113/04
[52] U.S. Cl. ................................ 260/141; 106/308 Q; 106/309; 106/316; 260/45.75 K; 260/143; 260/429.7; 424/226; 427/394; 427/395; 427/397

[58] Field of Search .............. 260/143, 141 AN, 429.7

[56] References Cited

PUBLICATIONS

Badische, Chemical Abstracts, vol. 54, 25541h (1960).
Fuse et al, Chemical Abstracts, vol. 65, pp. 9646-9647 (1966).
Pommer et al (I), Chemical Abstracts, vol. 82, #172912h (1975).
Pommer et al (II), Chemical Abstracts, vol. 83, #54625q (1975).

*Primary Examiner*—Floyd D. Higel
*Attorney, Agent, or Firm*—Keil & Witherspoon

[57] ABSTRACT

Triorganotin compounds of hydroxydiazenium oxides having a good fungicidal action, fungicides containing these compounds, and processes for their manufacture by reacting a triorganotin halide with a sodium or potassium salt of an N'-hydroxydiazenium oxide or with the N'-hydroxydiazenium oxide in the presence of an acid binder.

8 Claims, No Drawings

TRIORGANOTIN COMPOUNDS OF HYDROXYDIAZENIUM OXIDES AND FUNGICIDAL USES THEREOF

The present invention relates to new triorganotin compounds of hydroxydiazenium compounds and fungicides containing these compounds as active ingredients.

It is known (German 1,024,743, German Laid-Open Application DOS No. 2,336,290 and German Laid-Open Application Dos No. 2,341,882) to use salts of N-nitroso-N-cyclohexylhydroxylamine (NCH) for protecting wood against wood-destroying fungi such as Coniophora cerebella, Merulius lacrimans, and Lentinus lepideus. Of the compounds practically insoluble in water, the aluminum salt of NCH has particularly proved its worth. However, it is disadvantageous that fairly high concentrations are necessary to protect the wood. Even at high concentrations, the fungus Polystictus versicolor known as a hardwood destroyer is inadequately combated. It is a further drawback that the abovementioned NCH salts give relatively little protection against wood-populating bacteria.

It is further known that numerous fungi can be controlled with trialkyltin compounds, especially bis-(tri-n-butyltin)-oxide (Data Sheet No. 226, November 1961, Metal & Thermit Corp., New York).

We have now found that triorganotin compounds of hydroxydiazenium oxides of the formula

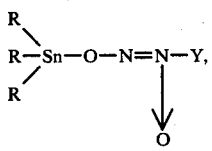

where the radicals R are identical or different and each denotes alkyl of from 1 to 12 carbon atoms, or phenyl, and Y denotes alkyl or cycloalkyl, are excellent fungicides and have a better action than the prior art trialkyltin compounds and NCH salts. Highly effective substituents R are preferably alkyl radicals of from 3 to 8 carbon atoms, e.g., propyl, butyl and octyl. A particularly suitable substituent for Y is the cyclohexyl radical. The new compounds are soluble in organic solvents, e.g., acetone, benzene, xylene, diesel oil, kerosine and paraffin oil, and may if desired be used in this solution together with wetting agents.

The following wood-destroying and wood-discoloring fungi and soft rot and mold fungi can be combatted with the new active ingredients: *Merulius lacrimans, Coniophora cerebella, Polystictus versicolor, Lentinus lepideus, Poria vaporaria, Lenzites trabea, Paxillus panoides, Fomus annosus, Stereum hirsutum, Pullularia pullulans, Aspergillus niger, Trichoderma viride, Cladosporium herbarum, Sclerophoma pityophila, Chaetomium globosum, Alternaria spec.,* and *Phoma Violacea.*

The active ingredients may be employed as microbicidally active components of oily wood preservatives. The preservatives are applied by treating the wood with them, e.g., by impregnation or coating. An oily wood preservative applied to the wood surface in amounts of from 50 to 200 ml/m² may contain from 0.2 to 5 wt% of the new active ingredients.

To achieve special effects, other insecticidally and/or fungicidally active compounds may be added to the oily wood preservatives. Examples are γ-hexachlorocyclohexane (Lindan), 6,7,8,9,10,10-hexachaloro-1,5,5a,6,9,9,a-hexahydro-6,9-methano-2,4,3-benzodioxathiepine-3-oxide (Endosulfan), 1-naphthyl-N-methylcarbamate (Carbaryl), pentachlorophenol, copper naphthenate, chlorinated naphthalenes, boron compounds, N-fluorodichloromethylthiophthalimide, N,N-dimethyl-N'-phenyl-(N'-fluorodichloromethylthio)-sulfamide and N-phenyl-N,N'-dimethyl-(N'-fluorodichloromethylthio)-sulfamide. With some mixtures of the compounds according to the invention with the abovementioned insecticides and fungicides synergism is observed.

The compounds according to the invention are suitable not only for use in wood protection, but may also be used as preservatives for technical products such as emulsion paints, leather, adhesives and paper.

The compounds according to the invention may be prepared by reacting a triorganotin halide of the formula

where R has the above meanings and X denotes halogen, with a sodium or potassium salt of N'-hydroxydiazenium oxide of the formula

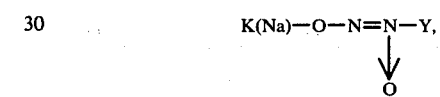

where Y has the above meanings, in accordance with the following reaction scheme:

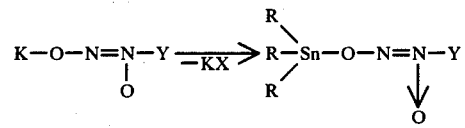

The reaction may be carried out with or without solvents. Suitable solvents are dimethylformamide, dimethyl sulfoxide, diethyl ether, dioxane, tetrahydrofuran and aromatic (optionally chlorinated) hydrocarbons such as benzene, toluene, xylene and chlorobenzene. The reaction temperature may vary over a wide range; generally, the process is operated at room or slightly elevated temperature (20° to 35° C.).

The free N'-hydroxydiazenium oxide may of course also be reacted with the triorganotin halide. In this case, the reaction is preferably carried out in the presence of an acid binder, e.g., sodium carbonate, pyridine and triethanolamine.

Generally, 1 mole of triorganotin halide is reacted with 1 mole of an alkali metal salt of N'-hydroxydiazenium oxide. The preparation of the active ingredients according to the invention is illustrated by the following example.

EXAMPLE 1

182 g of the potassium salt of N'-hydroxy-N-cyclohexyldiazenium oxide is added in portions to a solution of 326 g of tributyltin chloride in 500 ml of dimethyl sulfoxide, and the mixture is stirred for 20 hours at room temperature (20° C.). Water is then added to the mixture, extraction is carried out with diethyl ether, and the ether phase is washed with water and dried with anhydrous sodium sulfate. After concentration, there remains 375 g of an oily residue which distils at 150° to 160° C./0.1 to 0.2 mm Hg. The end product has the following formula:

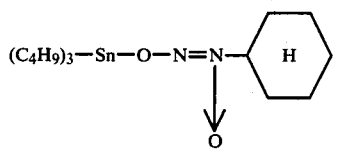

(1)

$C_{28}H_{56}N_4O_4Sn$

|  | C | H | N | Sn |
|---|---|---|---|---|
| Calc.: | 53.2 | 8.9 | 8.9 | 18.9 |
| Found: | 53.5 | 8.7 | 8.6 | 19.0 |

The following compounds were prepared analogously:

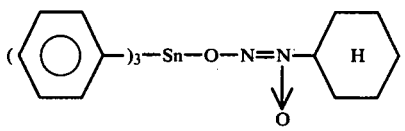

(2)

Viscous, undistillable oil which crystallizes slowly at room temperature.

$C_{24}H_{26}O_2N_2Sn$

|  | C | H | N | Sn |
|---|---|---|---|---|
| Calc.: | 58.4 | 5.3 | 5.7 | 24.1 |
| Found: | 58.2 | 5.2 | 5.4 | 24.2 |

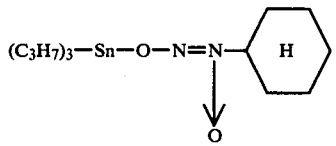

140° – 143° C./0.15 mm Hg
$C_{15}H_{32}N_2O_2Sn$

|  | C | H | $N_2$ | Sn |
|---|---|---|---|---|
| Calc.: | 46.0 | 8.2 | 7.2 | 30.4 |
| Found: | 45.9 | 8.3 | 7.2 | 30.0 |

The potassium salt of N'-hydroxy-N-cyclohexyl-diazenium oxide used as starting material is prepared as follows. A mixture of 3 l of cyclohexane and 0.5 l of concentrated aqueous hydrochloric acid is irradiated for 2 hours at 10° C. in a 4 l stirred flask equipped with a laterally immersed water-filled mercury vapor lamp (Philips HPK 125 W), a cooler, stirrer, thermometer and a gas-feed frit; simultaneously, 10 l of nitrogen monoxide is passed in per hour. After the lamp has been switched off, the aqueous phase is separated. The organic phase is freed from dissolved nitrogen monoxide by gassing with nitrogen, and is mixed with 200 ml of 20 wt% aqueous potassium hydroxide solution while stirring. The potassium salt of N'-hydroxy-N-cyclohexyl-diazenium oxide separates out. The product is very pure.

EXAMPLE 2

The fungicidal action of the new compounds was determined in accordance with the method of D. J. Dickinson published in the International Biodeterioration Bulletin, 10, 49–51, 1974, and entitled "A new technique for screening fungicide for wood preservation."

Filter paper discs having a diameter of 9 cm were impregnated with acetonic solutions containing from 0.006% to 0.2% (wt%) of active ingredient. After the solvent had evaporated, the paper discs were placed in glass dishes, moistened with 1 ml of nutrient solution and subsequently inoculated in the center with paper discs (diameter 18 mm) infected with the wood-destroying fungus Polystictus versicolor. To prevent the moist filter papers from drying, lids were placed on the glass dishes, which were then incubated at 22° C. for 14 days. The fungus growth was then assessed and the diameter of the fungus colonies was measured. The active ingredient concentration at which no more fungus growth occurs is given as the toxic concentration for the fungus under examination.

| | Determination of the fungicidal action on Polystictus versicolor | | | | | | | |
|---|---|---|---|---|---|---|---|---|
| | Diameter of fungus colonies in mm after 14 days - % active ingredient in solution | | | | | | | Toxic concentration |
| Active ingredient | 0.006 | 0.012 | 0.025 | 0.05 | 0.1 | 0.15 | 0.2 | (wt%) |
| 1 | 2 | 0 | 0 | 0 | 0 | 0 | 0 | 0.012 |
| 2 | 6 | 6 | 3 | 0 | 0 | 0 | 0 | 0.05 |
| 3 | 10 | 7 | 5 | 0 | 0 | 0 | 0 | 0.05 |
| aluminum salt of N-nitroso-N-cyclohexyl-hydroxylamine (German 1,024,743) | 45 | 26 | 18 | 13 | 10 | 8 | 7 | higher than 0.2 |
| $(C_4H_9)_3$-Sn-O-Sn-$(C_4H_9)_3$ (prior art compound for comparison purposes) | 12 | 10 | 6 | 6 | 2 | 0 | 0 | 0.15 |
| Control (untreated) | 72 | | | | | | | |

We claim:
1. A triorganotin compound of a hydroxydiazenium oxide of the formula

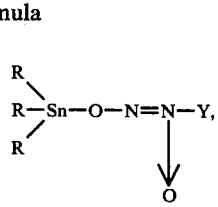

where the radicals R are identical or different and each denotes alkyl of from 1 to 12 carbon atoms, or phenyl, and Y denotes alkyl or cycloalkyl.
2. A compound as claimed in claim 1 wherein R in each occurrence is alkyl of 3–8 carbon atoms.
3. A compound as claimed in claim 1 wherein R in each occurrence is phenyl.

4. A compound as claimed in claim 1 wherein R in each occurrence is alkyl of 3–8 carbon atoms, and Y denotes cyclohexyl.

5. A compound as claimed in claim 1 wherein R in each occurrence is phenyl, and Y denotes cyclohexyl.

6. The tributyltin compound of N-cyclohexylhydroxydiazenium oxide.

7. The triphenyltin compound of N-cyclohexylhydroxydiazenium oxide.

8. The tripropyltin compound of N-cyclohexylhydroxydiazenium oxide.

* * * * *